United States Patent [19]

Kumbrant

[11] 4,197,745

[45] Apr. 15, 1980

[54] DISPOSABLE SAMPLING APPARATUS FOR OBTAINING SAMPLES FROM MOLTEN MATERIALS

[76] Inventor: Lars A. T. Kumbrant, Box 23, S-190 63 Örsundsbro, Sweden

[21] Appl. No.: 945,825

[22] Filed: Sep. 26, 1978

[30] Foreign Application Priority Data

Sep. 28, 1977 [SE] Sweden .................................. 7710870

[51] Int. Cl.² .............................................. G01N 1/12
[52] U.S. Cl. .............................................. 73/425.4 R
[58] Field of Search ...................... 73/425.4 R, DIG. 9

[56] References Cited

U.S. PATENT DOCUMENTS

| 3,455,164 | 7/1969 | Boyle | 73/DIG. 9 |
| 3,577,886 | 5/1971 | Wiese | 73/DIG. 9 |
| 4,046,016 | 9/1977 | Hackett | 73/425.4 R |

*Primary Examiner*—S. Clement Swisher
*Attorney, Agent, or Firm*—Witherspoon & Hargest

[57] ABSTRACT

Disposable sampling apparatus for drawing samples from melts by lowering thereof into the melt and comprising a mold embedded in a sand body, a tube constituting an inlet for the molten material into the mold and projecting out of the sand body, and a tubular sleeve surrounding a portion of the sand body and at least a portion of the inlet tube to the mold. The novelty features of the invention reside in the fact that the sleeve is arranged on a portion of the sand body adjacent the inlet tube and extends therefrom outwards around the inlet tube, and that there is a gas flow path through said sand portion from the recess formed between the inlet tube and the sleeve to an open portion of the sand body.

3 Claims, 2 Drawing Figures

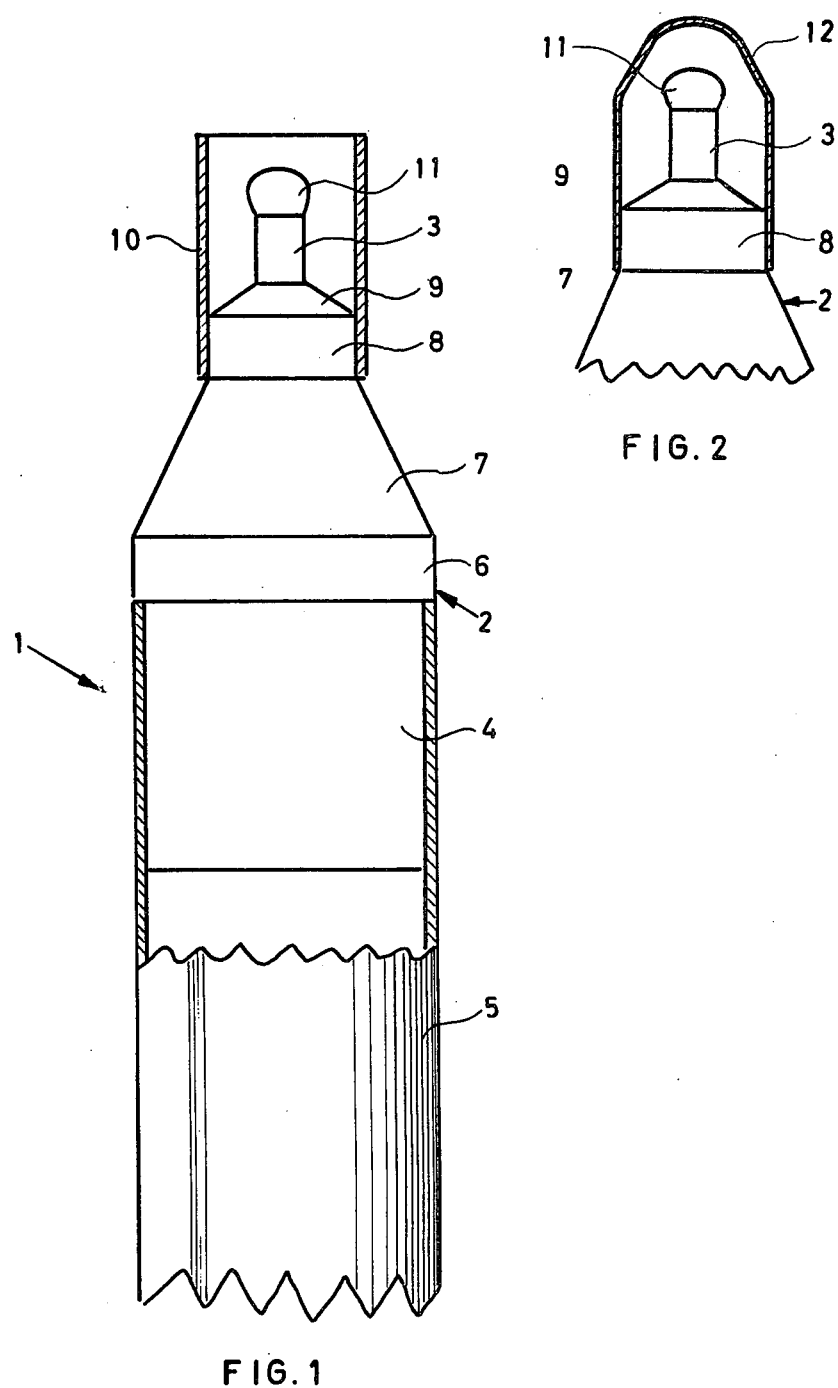

DISPOSABLE SAMPLING APPARATUS FOR OBTAINING SAMPLES FROM MOLTEN MATERIALS

The present invention relates to a sampling apparatus for obtaining samples from melt, or more precisely to a disposable sampling apparatus for obtaining samples from molten metals such as iron, steel or other metals and metal alloys.

Due to different reasons it has become more and more important that samples from molten metals may be obtained in a simple and quick way, e.g. when determining at what time a melt is ready for discharging. The costs of the sampling must not be too high, as this would injuriously effect the price of the metal in question. In the analysis field equipment has come out which in quick and simple ways produce the analysis results, whereas in the sampling field it has been difficult making sampling quicker and more simple without renouncing the quality of the samples. The new and carefully operating analysis equipment demands high quality samples to achieve results representative of the molten metal. Furthermore, the more and more rapid steel producing processes which have come into use demand greater rapidity between sampling and analysis result.

Previously known sampling apparatuses appear from e.g. U.S. Pat. Nos. 3,332,288 and 3,369,406. The first of these shows a very frequent type of sampling apparatus consisting of an evacuated glass tube provided with a weakening. This glass tube is meant to be lowered down into a melt, whereby the weakening bursts due to the heat and a sample from the melt is sucked into the tube.

It is obvious that such a tube is difficult to handle without breaking it and that it easily breaks when it bumps into slagg which flows on the melt. As said tube in the latter case sucks in remains of slagg, the sample will not with certainty be representative of the melt.

An attempt has been made to protect said known sampling tube during its entering into the melt by means shown in the latter of the mentioned patent specifications. However, the sampling apparatus designed according to this patent specification is of a very complex construction, and for that reason, such a sampling appartus will be far too expensive to be of common use. The sampling apparatus in accordance with this patent specification is provided with a cap covering the inlet tube to the sampling chamber. This construction shows, however, a substantial drawback in the fact that the air entrapped inside the protecting cap might lack a possibility to be vented when subjected to the expansion caused by the heat of the melt. This gives rise to the fact that the protecting cap might be burst making the sampling apparatus unusable. This problem is well-known and due to this fact a vent orifice is made in the protecting cap. However, there is a great risk for the fact that said vent orifice is clogged and accordingly, there is all the time a risk for bursting of the protecting cap.

These known sampling apparatuses have the common feature that they use sampling tubes which on one hand require tooling to achieve a weakening, evacuating and sealing and on the other hand are very difficult to control whether they are in working order or not, i.e. to control that air has not leaked in through e.g. an invisible crack and thus made the sampling apparatus useless.

The object of the present invention is to remove the drawbacks of previously known sampling apparatuses and to provide a disposable sampling apparatus which is quick and simple to use and presents high quality samples respresentative of the melt, in addition to which it is inexpensive to produce.

The above mentioned object is obtained by means of a disposable sampling apparatus as defined in the claims from which also the features especially characterizing the invention are clear.

The invention will be closer described in the following with reference to the attached drawing, in which FIG. 1 is a schematic, part-sectional view of a sample apparatus in accordance with the invention, and FIG. 2 is a broken away, part-sectional view through a second embodiment of the invention.

The disposable sampling apparatus 1 in accordance with the present invention comprises a sampling mold or the like embedded in a sand body 2 and having a glass tube 3 protruding from the sand body 2. In the shown embodiment the sand body 2 is of circular cross-section but also other cross-sectional shapes are possible without diverting from the inventive concept.

The sand body 2 shows a rather broad base portion 4 onto which a cardboard tube is threaded. This cardboard tube 5 is intended to constitute the handle when the sampling apparatus is to be lowered into a melt. The tube 5 may be made of other material than cardboard and it is not necessarily of disposable type.

The base portion 4 is provided with a circumferential shoulder 6 constituting a stop for the handle tube 5 when this is threaded onto the sampling apparatus 1. From the shoulder 6 the sand body 2 is in the shape of a truncated cone 7 and runs thereafter into a cylindrical portion 8. The cylindrical portion 8 terminates in a curved end surface 9 out of the central portion of which the glass tube 3 extends.

It is a desire to keep this protruding glass tube 3 protected during storing and transporting and when the sampling apparatus is lowered into a melt. For this reason a sleeve 10 is threaded onto the cylindrical portion 8 which sleeve 10 preferably extends a short distance outside the outer end of the glass tube 3. Said sleeve 10 may be made from cardboard or other suitable material.

A metal slagg cover 11 is preferably placed over the end of the glass tube 3. A further cover may be placed over the open end of the sleeve 10. The outer cover has a function during transportation and storing of the sampling apparatus so that it is impossible for any object to engage and destroy the protruding glass tube 3. The outer cover is also a mechanical protection for the glass tube 3 while the sampling apparatus is brought through the slagg layer that is on melts. However, this cover is molten in a very early stage simultaneously as the sleeve 10 is burned away. Thereafter the cover 11 is molten away and the molten metal can enter the sampling apparatus. Due to the double covers the sampling apparatus 1 can be brought accurately down into the molten metal before the sample is drawn.

As a substitute for or complementary to the slagg cover 11 an outer cover may be, as mentioned, placed over the open end of the sleeve 10. Thereby a closed chamber is formed which would show the risk of bursting previously mentioned. However, the sand body 2 is very gas pervious. Further, due to the fact that the cylindrical portion 8 is rather short or that anyhow, the sleeve 10 surrounds only a short part of this portion the gases when expanding within the sleeve 10 may flow through the porous sand body through the surface 9 around the glass tube 3 and out through the part of the sand body placed behind the socket 10, e.g. through the part 7 which in the shown embodiment is in the shape of a truncated cone. In this construction there is no risk for clogging of vent orifice and the through-flow surface is so large that no pressure collection takes place anywhere which would be sufficient to give rise to even crack formation.

In the embodiment shown in FIG. 2 the socket 10 has been substituted by a dome shaped cap 12. This cap 12 substitutes the socket 10 and the outer cover, if any, and may also substitute the slagg cover 11. Neither in this embodiment there are no special measures to take into consideration in order to prevent that the cap is burst by expanding gas but the gas will flow through the sand body as previously mentioned.

What I claim is:

1. A disposable sampling apparatus for drawing samples from melts by lowering said apparatus into the melt comprising a sand body having attached at one end thereof a handle, said sand body being very pervious to gas and having embedded therein a mold including an inlet tube projecting from the other end of said sand body, and a tubular sleeve attached to said other end and spaced from said handle to provide an open portion of said sand body between said sleeve and said handle, the width of said open portion nearest said one end of said sand body being greater than the width of said open portion nearest said other end of said sand body such that said open portion is in the shape of a truncated cone, said sleeve extending from said other end and around said inlet tube to provide a recess between said sleeve and said inlet tube, and a gas flow path extending from said recess through said sand body to said open portion thereof.

2. Sampling apparatus in accordance with claim 1, characterized by the fact that an outer cover is placed over the open end of the sleeve.

3. Sampling apparatus in accordance with claim 1, characterized by the fact that the sleeve is constituted by a dome shaped cap.

* * * * *